United States Patent
Choi et al.

(10) Patent No.: US 10,267,676 B2
(45) Date of Patent: Apr. 23, 2019

(54) NON-POWER-DRIVEN PHOTOMETER INCLUDING MULTIPLE NARROW-ANGLE PHOTORECEIVERS

(71) Applicant: Kyu Young Choi, Jeju-do (KR)

(72) Inventors: Kyu Young Choi, Jeju-do (KR); Edward J. Milton, Hampshire (GB)

(73) Assignee: Kyu Young Choi, Jeju-Do (KR)

( * ) Notice: Subject to any disclaimer, the term of this patent is extended or adjusted under 35 U.S.C. 154(b) by 160 days.

(21) Appl. No.: 15/529,216

(22) PCT Filed: Nov. 23, 2015

(86) PCT No.: PCT/KR2015/012603
§ 371 (c)(1),
(2) Date: May 24, 2017

(87) PCT Pub. No.: WO2016/085216
PCT Pub. Date: Jun. 2, 2016

(65) Prior Publication Data
US 2017/0363463 A1   Dec. 21, 2017

(30) Foreign Application Priority Data

Nov. 24, 2014  (KR) .......................... 10-2014-0164773

(51) Int. Cl.
*G01J 1/42*  (2006.01)
*G01J 1/04*  (2006.01)
(Continued)

(52) U.S. Cl.
CPC .............. *G01J 1/42* (2013.01); *G01J 1/0266* (2013.01); *G01J 1/0271* (2013.01);
(Continued)

(58) Field of Classification Search
CPC ...... G01J 1/0425; G01J 1/42; G01J 2001/428; G01J 3/0289; G01J 3/0291
(Continued)

(56) References Cited

U.S. PATENT DOCUMENTS 4,710,618 A * 12/1987 Matsumoto ........... G01S 3/7862
126/573

FOREIGN PATENT DOCUMENTS

JP   2003-232676 A   8/2003
JP   2005-189088 A   7/2005
(Continued)

*Primary Examiner* — Que Tan Le
(74) *Attorney, Agent, or Firm* — Husch Blackwell LLP

(57) ABSTRACT

A non-power-driven photometer is provided, the photometer comprising: a body; and multiple narrow angle photoreceivers (narrow angle probes) formed in the body, wherein the multiple narrow angle probes receive light in the atmosphere, which is incident over a range of different azimuth angles, and allow the characteristics of the atmosphere to be analyzed with reference to the relationship between the received light and the azimuth angle of the narrow angle probe corresponding to the received light. According to the present invention, since the photometer is driven without being supplied with power, light intensity measurement can be performed in a short time. Further, since light intensity measurement can be performed with no movement or only a short-distance movement of a vehicle or airplane equipped with the photometer, the problem of errors caused by differences in the time and location of measurement can be prevented.

13 Claims, 6 Drawing Sheets

(51) Int. Cl.
  *G01J 1/02*     (2006.01)
  *G01J 3/02*     (2006.01)
  *G01J 1/58*     (2006.01)
  *G01N 21/17*    (2006.01)

(52) U.S. Cl.
  CPC ........... *G01J 1/0425* (2013.01); *G01J 1/0474* (2013.01); *G01J 1/58* (2013.01); *G01J 3/0289* (2013.01); *G01J 3/0291* (2013.01); *G01J 2001/428* (2013.01); *G01J 2001/4266* (2013.01); *G01N 2021/1795* (2013.01)

(58) Field of Classification Search
  USPC ..................................................... 250/203.4
  See application file for complete search history.

(56) References Cited

FOREIGN PATENT DOCUMENTS

| | | |
|---|---|---|
| JP | 2008-256506 A | 10/2008 |
| KR | 10-0940479 B1 | 2/2010 |
| KR | 10-1000267 B1 | 12/2010 |

* cited by examiner

WHEN NOT SHAKEN

WHEN SHAKEN

1

NON-POWER-DRIVEN PHOTOMETER INCLUDING MULTIPLE NARROW-ANGLE PHOTORECEIVERS

CROSS REFERENCE TO RELATED APPLICATIONS

This application is a U.S. National Phase Application of International Application No. PCT/KR2015/012603 filed on Nov. 23, 2015, which claims the benefit of priority from Korean Patent Application 10-2014-0164773 filed on Nov. 24, 2014. The disclosures of International Application No. PCT/KR2015/012603 and Korean Patent Application 10-2014-0164773 are incorporated herein by reference.

FIELD OF THE INVENTION

The present invention relates to a non-power driven photometer including multiple photoreceivers, and more particularly, to the non-power driven photometer with multiple narrow-angle probes that receive lights entering from different ranges of individual azimuthal angles.

BACKGROUND OF THE INVENTION

A sun photometer is a device that measures amount and distribution of light coming from the sky. The sun photometer may estimate the state of the atmosphere through the information on measured amount and distribution of light. Herein, the light as an object of measurement may include lights by reflection, refraction, and scattering. For reference, they are together called "scattered lights" in this specification.

The state of the atmosphere may show characteristic patterns of atmospheric particles. The sun photometer may estimate characteristics of the atmospheric particles through light distribution patterns. For example, light reflecting characteristics may depend on characteristics of the atmospheric particles. The characteristics of particles may include particle sizes, particle shapes, transmittance, etc.

To determine the state of the atmosphere, a sun tracking method and a sky scanning method may be used.

The sun tracking is a method that measures amount and distribution of light, toward the sun. Information measured by the sun tracking includes atmospheric transmittance, aerosol optical depth, Angstrom exponent, aerosol extinction, moisture ($H_2O$), ozone ($O_3$), etc.

The sky scanning is a method of scanning the whole sky regardless of the sun. It may discretely scan the sky from different ranges of azimuthal angles. Herein, the angle toward the sun may be excluded. To scan the different ranges of azimuthal angles, a motor may rotate probes to a specific azimuthal angle. Information measured by the sky scanning includes scattering phase function, asymmetry parameter, aerosol size distributions, aerosol sphericity, aerosol absorption, cloud optical properties, etc.

One of measurement methods using the sun tracking and the sky scanning is a method by installing the sun photometer in an aircraft, etc. For example, when an aircraft on the ground measures a state of atmosphere such as a pattern of atmospheric scattering through ground observations, the state of all layers of the atmosphere may be measured. More specifically, if the distance from the surface of the earth to the sun is L, and if an aircraft at an altitude of $\Delta L$ measures a state of atmosphere through aerial observation, the state of all the layers of the atmosphere corresponding to a height of $L'$, where $L'=L-\Delta L$ may be measured. In addition, if the

2 aircraft measures a state of the atmosphere corresponding to the height of $L'$ which varies as $\Delta L$, the states of the atmosphere at each altitude may be found. The conventional photometer is shown in FIG. 1. By referring to FIG. 1, the photometer is illustrated on the top left and the state of the photometer being installed in an aircraft is illustrated.

However, the measurement method by using such an aircraft has a problem that it takes more time and errors in measurement occur as a position of the aircraft changes. Specifically, as the sky scanning may be operated by a motor, calibration is required due to changes in measuring angles depending on rotations of the motor and changes in measuring positions depending on movements of the aircraft. In other words, by referring to FIG. 1, the photometer shown on the top left may be rotated by a motor while installed in the aircraft. For example, if 100 seconds are required to scan the whole sky while the azimuthal angles are changed by using the motor, the aircraft may move a distance of roughly 10 kilometers for 100 seconds. Besides, even under the sun tracking, the photometer installed in the aircraft as shown in FIG. 1 could track the sun while being rotated by the motor. While angles of probes are changed by the motor to track a position of the sun, the aircraft could move a considerable distance and errors in measurement could occur.

Accordingly, the present inventor came to develop non-power driven technology that allows intensity of light to be measured by kinematically placing multiple probes that receive or detect lights entering from different ranges of individual azimuthal angles.

SUMMARY OF THE INVENTION

It is an object of the present invention to solve all problems stated above.

It is another object of the present invention to relatively accurately measure intensity of light without power within a shorter time by using a photometer including multiple probes that detect lights entering from different ranges of individual azimuthal angles.

It is still another object of the present invention to allow amount or distribution of light to be relatively more accurately measured by using multiple probes placed not only on surfaces of an upper hemisphere but also on surfaces of a lower hemisphere even while a vehicle or an aircraft on which the photometer is installed is leaning to one side.

In accordance with one aspect of the present invention, there is provided a non-power driven photometer, including: a body; and multiple narrow-angle probes formed on the body; wherein the multiple narrow-angle probes receive lights entering from different ranges of individual azimuthal angles through atmosphere, wherein the multiple narrow-angle probes allow total amount of the received lights to be analyzed or allow azimuthal characteristics of the atmosphere to be analyzed by referring to relationships between the received lights and the azimuthal angles of the narrow-angle probes corresponding to the received lights, and wherein the lights include at least some of direct lights and indirect lights.

DETAILED DESCRIPTION OF THE PREFERRED EMBODIMENTS

Figure 1:
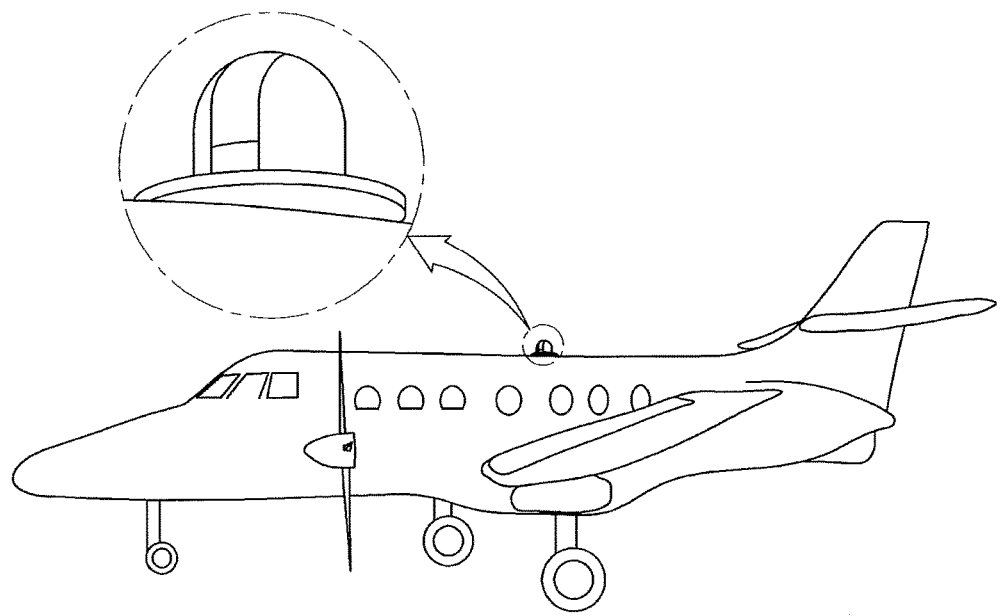
FIG. 1 is a drawing representing an external appearance of a conventional photometer and a state of the conventional photometer being installed in an aircraft.

Detailed explanations of the present invention explained below refer to attached drawings that illustrate specific embodiment examples of this present that may be executed. These embodiments are described in sufficient detail to enable those skilled in the art to practice the invention. It is to be understood that the various embodiments of the present invention, although different, are not necessarily mutually exclusive. For example, a particular feature, structure, or characteristic described herein in connection with one embodiment may be implemented within other embodiments without departing from the spirit and scope of the present invention. In addition, it is to be understood that the position or arrangement of individual elements within each disclosed embodiment may be modified without departing from the spirit and scope of the present invention. The following detailed description is, therefore, not to be taken in a limiting sense, and the scope of the present invention is defined only by the appended claims, appropriately interpreted, along with the full range of equivalents to which the claims are entitled. In the drawings, like numerals refer to the same or similar functionality throughout the several views. To make those in the art skilled in the art from being easily executed, detailed explanation will be made by referring to drawings attached in relation to desirable example embodiments.

Configuration of a Photometer

Figure 2:
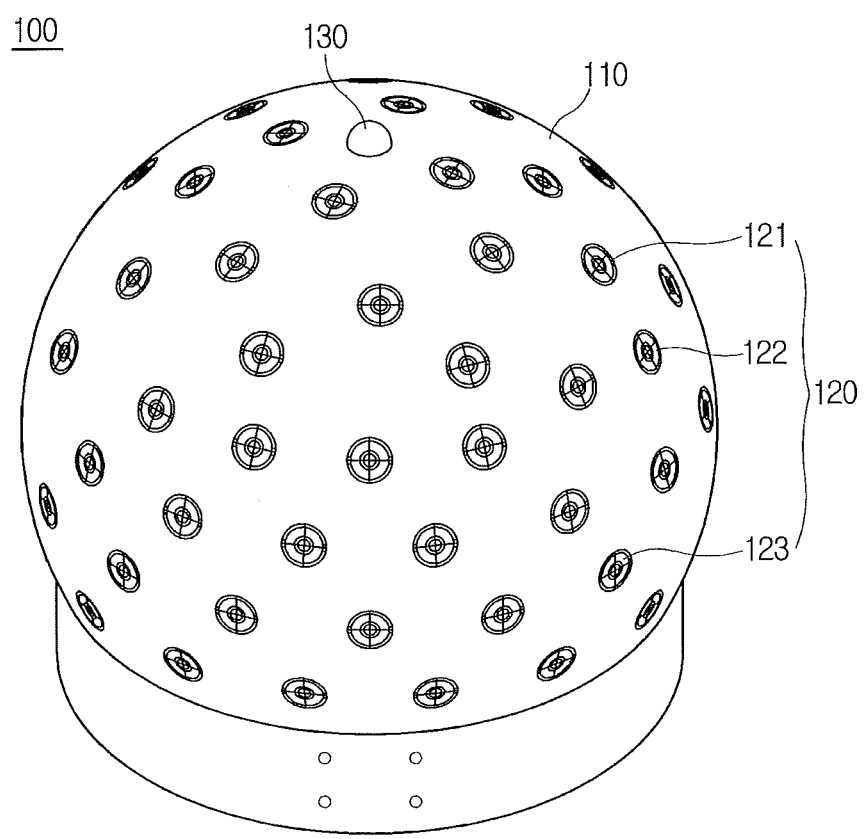
FIG. 2 is a diagram showing an external appearance of the photometer in accordance with the present invention.

FIG. 2 is a drawing illustrating an external appearance of a photometer in accordance with the present invention.

As illustrated in FIG. 2, the photometer 100 may include a body 110 and multiple narrow-angle probes 120. In FIG. 2, as parts of the multiple narrow-angle probes 120, a first narrow-angle probe 121, a second narrow-angle probe 122, a third narrow-angle probe 123, etc. are shown. Additionally, other multiple narrow-angle probes in a similar fashion are illustrated.

Figure 5:
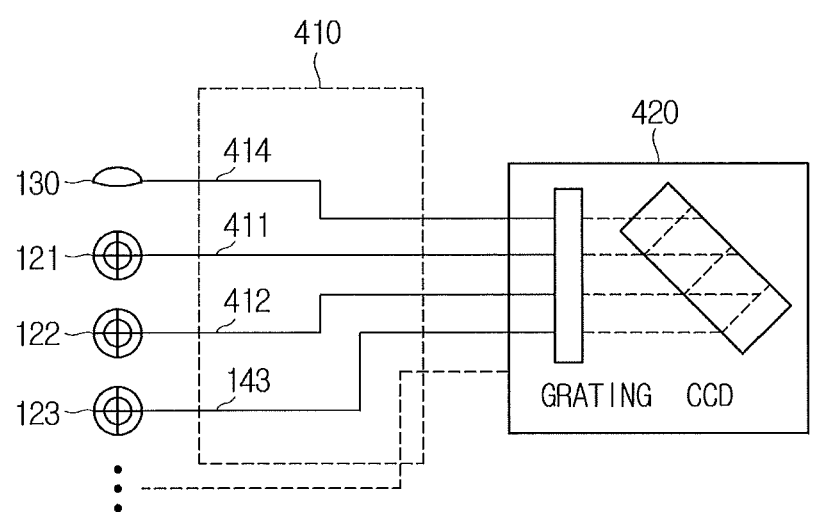
FIG. 5 illustrates a state of the photometer in accordance with one example embodiment of the present invention being connected with a sensor.

In accordance with one example embodiment of the present invention, a narrow-angle probe may be a unit that detects lights entering from atmosphere or the sun through angle of narrow ranges. The multiple narrow-angle probes may receive lights entering at different ranges of individual azimuthal angles. The narrow-angle probe may receive a light which may be a direct light or an indirect light such as a scattered light, entering at an angle within a certain value from the perpendicular to the narrow-angle probe or its lens, and may detect the light as the case may be. For example, as shown in FIG. 5, if each sensor 420 which is connected with each narrow-angle probe through each of optical fibers 410 detects a light, the narrow-angle probe may simply have a function of receiving a light without detecting anything, or as another case, individual small sensors (not illustrated) for individual narrow-angle probes could be installed at individual small spaces formed near the corresponding narrow-angle probes inside the body 110 to connect the sensors with the probes without connections through the optical fibers 410. Meanwhile, depending on characteristics of the narrow-angle probes, each of the narrow-angle probes could receive lights entering at each corresponding range of angles within 3° from the perpendicular to the narrow-angle probe or its lens but they are not limited to this.

In accordance with one example embodiment of the present invention, the photometer 100 may work without power by using the multiple narrow-angle probes. In other words, the photometer 100 may not include any part which is operated by a motor and the multiple narrow-angle probes may have fixed positions with respect to the photometer 100. Because there are multiple narrow-angle probes, lights entering at different ranges of individual azimuthal angles may be received and detected at the same time by the multiple narrow-angle probes, and reception and detection of lights within wide ranges may be performed at the same time or within a faster time without any driving part such as a motor.

In accordance with one example embodiment of the present invention, the multiple narrow-angle probes may be placed on the body 110. To receive lights entering from all directions, the multiple narrow-angle probes may be placed uniformly on the body 110. For example, distances among the narrow-angle probes on the surface of the body 110 may be the same.

In accordance with one example embodiment of the present invention, the body 110 may be dome-shaped or skydome-shaped to make the multiple narrow-angle probes placed uniformly. Besides, the body 110 may have a shape which allows the multiple narrow-angle probes placed on the surface of the body 110 to receive and detect lights entering from each corresponding range of the angles.

In accordance with one example embodiment of the present invention, the photometer 100 may further include at least one wide-angle probe 130. The wide-angle probe 130 may detect lights entering from the whole sky. In short, the wide-angle probe 130 may scan lights entering from the whole sky at a time. The wide-angle probe 130 may be placed on the top of the body 110 or at a place perpendicular to the center of the body 110. As illustrated in FIG. 2, the wide-angle probe 130 may protrude from the surface of the body 110 in a shape of hemisphere or convex lens to receive lights entering from several directions.

In addition, the wide-angle probe 130 in accordance with one example embodiment of the present invention may include a diffuser that scatters lights entering the wide-angle probe 130 and may be comprised of ground glass, etc. as one example.

In accordance with one example embodiment of the present invention, the photometer 100 may detect lights, entering the photometer 100 through the multiple narrow-angle probes 120 and the wide-angle probes 130, at a specific sampling rate.

Figure 3:
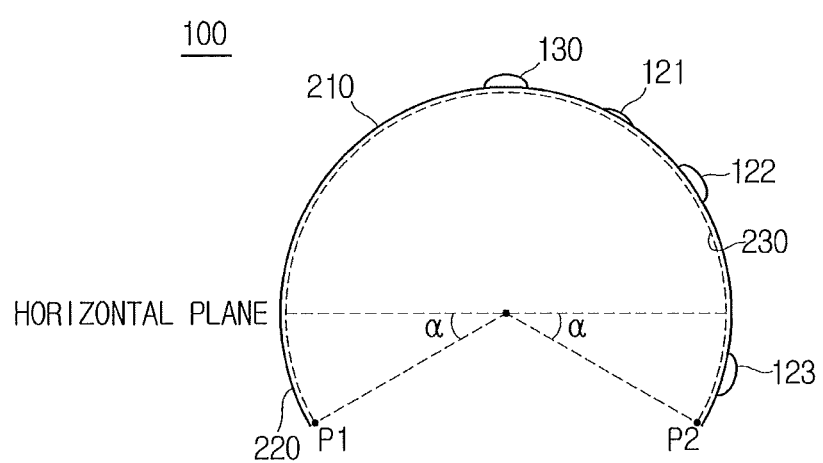
FIG. 3 is a cross-section of the photometer in accordance with one example embodiment of the present invention.

FIG. 3 represents a cross-section of the photometer in accordance with one example embodiment of the present invention.

Just as explained above by referring to FIG. 2, the body 110 may have a shape suitable for making the multiple narrow-angle probes receive lights entering at different angles.

As illustrated in FIG. 3, the body 110 may have a shape of partial sphere 230 including an upper hemisphere 210 as its part. In other words, the body 110 may have a shape of partial sphere created by cutting a whole sphere with a virtual horizontal plane located below from the center of the sphere and the body 110 may include the upper hemisphere 210 and at least a part 220 of the lower hemisphere whose lower part is horizontally cut. In FIG. 3, an angle between a first straight line connecting the bottommost point of the cut part, P1 or P2, of the partial sphere 230 with the center of the sphere and a second straight line corresponding to the diameter of the sphere included in the horizontal plane passing through the center of the sphere is illustrated as α. For instance, α may be 15°.

In accordance with one example embodiment of the present invention, in case the photometer 100 is parallel to the horizontal plane, the upper hemisphere 210 may be a portion for receiving and detecting lights entering from the upper side of the horizontal plane, and may include not only the wide-angle probe 130 but also the first narrow-angle probe 121, the second narrow-angle probe 122, etc. The part 220 of the lower hemisphere exists on the lower side of the horizontal plane passing through the center of the sphere and includes the third narrow-angle probe 123, etc. If the photometer 100 receives the lights while keeping its horizontal position, it may not be necessary to receive the lights with the third narrow-angle probe 123. However, there are many cases that the photometer 100 is difficult to be kept in the horizontal position due to turbulence during a flight of a moving object such as an aircraft or a vehicle on which the photometer 10 is installed. In such cases, the third narrow-angle probe 123, etc. may happen to move above the horizontal plane instead of below. Even though such a moving object is being shaken, another set of the multiple narrow-angle probes may be still arranged uniformly on areas above from the horizontal plane and allow the another set of the multiple narrow-angle probes to receive lights from the atmosphere and detect characteristics of the atmosphere. For reference, it is assumed that the moving object is shaken at an angle no more than a degree from the horizontal plane.

Figure 4A:
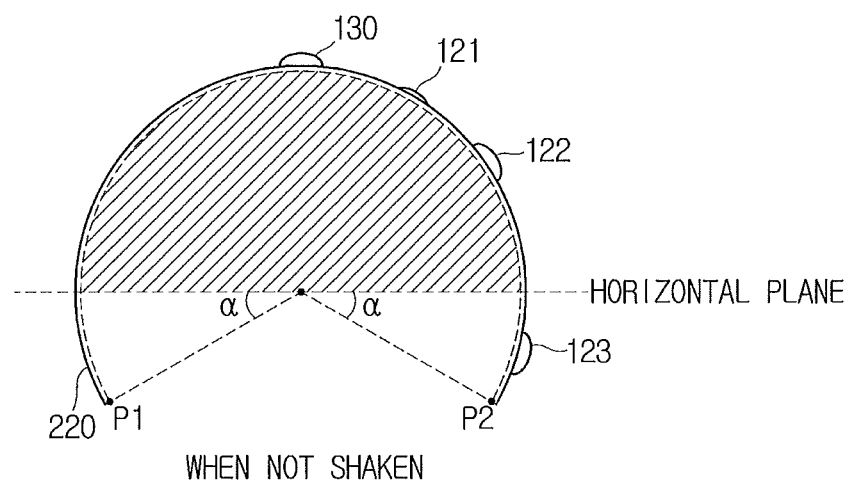
FIGS. 4A and 4B show the operating state of a narrow-angle probe, respectively, performing measurement while the photometer in accordance with one example embodiment of the present invention is not shaken and when it is shaken.

FIG. 4A shows the operating state of narrow-angle probes performing measurement when the photometer is not being shaken. In this regard, the narrow-angle probes placed above the horizontal plane, i.e., the narrow-angle probes in the shaded areas in FIG. 4A, may receive and detect lights from the atmosphere.

Figure 4B:
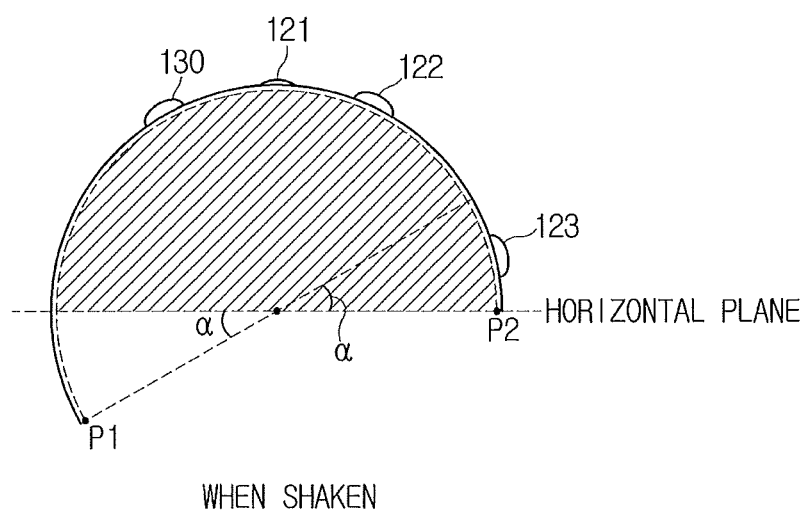

Besides, FIG. 4B shows the operating state of narrow-angle probes performing measurement when the photometer is being shaken. Under the case in which the object is shaken at an angle of α, the narrow-angle probes still uniformly exist on areas above the horizontal plane, i.e., the narrow-angle probes in the shaded areas shown in FIG. 4B. It is because the narrow-angle probes below the horizontal plane on the bottom right of FIG. 4A move to areas above on FIG. 4B due to shaking. Accordingly, the state of the atmosphere can be detected based on information received by the narrow-angle probes in the shaded areas shown in FIG. 4B, even when shaken.

FIG. 5 illustrates a sensor in accordance with one example embodiment of the present invention.

In accordance with one example embodiment of the present invention, the photometer 100 may further include optical fibers 410 and at least one sensor 420.

In accordance with one example embodiment of the present invention, the sensor 420 may detect spectral characteristics. The sensor 420 may be a multi-channel spectrometer that may measure hyperspectral visible and near-infrared spectra. For example, the sensor 420 may detect lights with wavelengths from 470 nm to 915 nm.

In accordance with one example embodiment of the present invention, the sensor 420 may detect spectral characteristics of the lights entering the multiple narrow-angle probes. The individual multiple narrow-angle probes may be connected with the sensor 420 through the individual optical fibers 410. In other words, signals created by narrow-angle probes may be transmitted to the sensor 420 through the optical fibers 410. In FIG. 5, among the multiple narrow-angle probes, the first narrow-angle probe 121, the second narrow-angle probe 122, and the third narrow-angle probe 123 are illustrated and the narrow-angle probes are connected with the sensor 420, respectively through a first optical fiber 411, a second optical fiber 412, and a third optical fiber 413.

In addition, a signal created by the wide-angle probe 130 may be transmitted to the sensor 420 through another optical fiber 414, wherein the signal created may represent the total amount of lights.

In accordance with one example embodiment of the present invention, the sensor 420 may perform a function of a prism and charge-coupled device (CCD). In other words, the sensor 420 may create a result of diffusing lights entering through multiple optical fibers as if the prism diffused lights to the CCD. That is, the sensor 420 may include a volume-phase holographic grating spectrometer. The sensor 420 may be configured to make signals transmitted from the multiple optical fibers cause minimal cross talk. By way of the prism function, the individual signals in the sensor 420 from the multiple optical fibers may appear at specific locations of the CCD. For example, a signal transmitted from one optical fiber may create one vertical line in the sensor 420. That is, multiple vertical lines appearing in the CCD may represent respective signals transmitted from the individual narrow-angle probes. The sensor 420 could be configured to make the vertical lines created by signals transmitted through the multiple optical fibers spaced out as far as possible but it is not limited to this.

In accordance with one example embodiment of the present invention, contrary to the illustration, the individual narrow-angle probes may have separate individual sensors that measure intensity of lights received.

In accordance with the present invention, the photometer may be operated without power.

In accordance with the present invention, the measurement of states of the atmosphere may be achieved within a short time because lights are received from multiple ranges of azimuthal angles at a time by using multiple narrow-angle probes.

In accordance with the present invention, even while a vehicle or an aircraft in which the photometer is installed is tilted, an effect of the accurate measurement of the state of the atmosphere will be achieved.

The embodiments of the present invention as explained above can be implemented in a form of executable program command through a variety of computer means recordable to computer readable media. The computer readable media may include solely or in combination, program commands, data files, and data structures. The program commands recorded to the media may be components specially designed for the present invention or may be usable to a skilled person in a field of computer software. Computer readable record media include magnetic media such as hard disk, floppy disk, and magnetic tape, optical media such as CD-ROM and DVD, magneto-optical media such as floptical disk and hardware devices such as ROM, RAM, and flash memory specially designed to store and carry out programs. Program commands include not only a machine language code made by a compiler but also a high-level code that can be used by an interpreter etc., which is executed by a computer. The aforementioned hardware device can work as more than a software module to perform the action of the present invention and they can do the same in the opposite case.

As seen above, the present invention has been explained by specific matters such as detailed components, limited embodiments, and drawings. While the invention has been shown and described with respect to the preferred embodiments, it, however, will be understood by those skilled in the art that various changes and modification may be made without departing from the spirit and scope of the invention as defined in the following claims.

Accordingly, the thought of the present invention must not be confined to the explained embodiments, and the following patent claims as well as everything including variants equal or equivalent to the patent claims pertain to the category of the thought of the present invention.

What is claimed is:

1. A non-power driven photometer, comprising:
a body; and
multiple narrow-angle probes formed on the body;
wherein the multiple narrow-angle probes receive lights entering from different ranges of individual azimuthal angles through atmosphere, wherein the multiple narrow-angle probes allow total amount of the received lights to be analyzed or allow azimuthal characteristics of the atmosphere to be analyzed by referring to relationships between the received lights and the azimuthal angles of the narrow-angle probes corresponding to the received lights, and wherein the lights include at least some of direct lights and indirect lights.

2. The photometer of claim 1, wherein the multiple narrow-angle probes have fixed positions on the photometer.

3. The photometer of claim 1, wherein, based on one horizontal plane which is a virtual plane that pass through diameters of the body horizontally, the narrow-angle probes are placed on an area of the body above the horizontal plane and on an area of the body below the horizontal plane within a degree from the horizontal plane.

4. The photometer of claim 3, wherein the angle of a degrees is decided by referring to information on an extent of fluctuation of a moving object on which the body is installed.

5. The photometer of claim 3, wherein the body includes an upper hemisphere located on the area above the horizontal plane and at least part of a bottom hemisphere located on the area below the horizontal plane.

6. The photometer of claim 1, wherein the multiple narrow-angle probes are placed on the body at regular intervals.

7. The photometer of claim 1, further comprising: a wide-angle probe that receives the lights coming from the whole sky.

8. The photometer of claim 7, wherein the wide-angle probe includes a diffuser that diffuses the lights coming into the wide-angle probe.

9. The photometer of claim 7, wherein the wide-angle probe is formed to protrude with respect to a surface of the body.

10. The photometer of claim 7, wherein the wide-angle probe is connected with a sensor through an optical fiber and the sensor detects and analyzes the lights received through the wide-angle probe.

11. The photometer of claim 7, wherein the wide-angle probe is connected with a sensor and wherein the sensor which is embedded in a space corresponding to the wide-angle probe among internal space of the body detects and analyzes the lights received through the wide-angle probe.

12. The photometer of claim 1, wherein the individual narrow-angle probes are connected with one or more sensors through individual optical fibers and the sensors detect and analyze the lights received through the individual narrow-angle probes.

13. The photometer of claim 1, wherein the individual narrow-angle probes are connected with one or more sensors and wherein the specific sensors embedded in individual spaces corresponding to the individual narrow-angle probes among internal space of the body detect and analyze the lights received through the individual narrow-angle probes.

* * * * *